(12) United States Patent
Obukowho

(10) Patent No.: US 9,420,862 B2
(45) Date of Patent: *Aug. 23, 2016

(54) NEUTRALIZING HAIR COMPOSITION

(75) Inventor: Patrick Obukowho, Fords, NJ (US)

(73) Assignee: SPARTAN BRANDS, INC., New York, NY (US)

( * ) Notice: Subject to any disclaimer, the term of this patent is extended or adjusted under 35 U.S.C. 154(b) by 543 days.

This patent is subject to a terminal disclaimer.

(21) Appl. No.: 12/760,108

(22) Filed: Apr. 14, 2010

(65) Prior Publication Data

US 2011/0253160 A1    Oct. 20, 2011

(51) Int. Cl.
| | | |
|---|---|---|
| *A45D 7/04* | (2006.01) |
| *A61Q 5/04* | (2006.01) |
| *A61Q 5/12* | (2006.01) |
| *A61K 8/36* | (2006.01) |
| *A61K 8/41* | (2006.01) |

(52) U.S. Cl.
CPC . *A45D 7/04* (2013.01); *A61K 8/361* (2013.01); *A61K 8/416* (2013.01); *A61Q 5/04* (2013.01); *A61Q 5/12* (2013.01)

(58) Field of Classification Search
CPC ..... A61K 8/43; A61K 8/922; A61K 2800/21; A61K 2800/413; A61K 2800/88; A61K 2800/884; A61K 8/06; A61K 8/062; A61K 8/19; A61K 8/31; A61K 8/355; A61K 8/361; A61K 8/416; A61K 8/8147; A61K 8/84
See application file for complete search history.

(56) References Cited

U.S. PATENT DOCUMENTS

| | | | | |
|---|---|---|---|---|
| 4,347,237 | A |   | 8/1982 | Evenstad |
| 4,373,540 | A | * | 2/1983 | de la Guardia ............... 132/204 |
| 5,565,216 | A | * | 10/1996 | Cowsar et al. ................ 424/704 |
| 6,007,585 | A | * | 12/1999 | Syed et al. ........................ 8/432 |
| 6,562,328 | B2 | * | 5/2003 | Pereira et al. ............. 424/70.28 |
| 6,562,356 | B2 | * | 5/2003 | Verite et al. .................. 424/401 |
| 2009/0074683 | A1 | * | 3/2009 | Nguyen et al. .................. 424/59 |

OTHER PUBLICATIONS

"Biomimetic hair care ingredient from Croda", Cosmetic design. com, published Jan. 13, 2005. Accessed online Jun. 29, 2012.*
"Cutissential 18-MEA 40" Product Data Sheet, Croda Personal Care. Accessed online Jun. 29, 2012.*
"The HLB System a time-saving guide emulsifier selection", ICI Americas, Inc. http://www.firp.ula.ve/archivos/historicos/76 Book HLB ICI.pdf, accessed online Feb. 5, 2013.
Croda specialty ingredients for personal care, second edition. Copyright Nov. 2005, pp. 1-62.
Croda Personal Care, Crussential 18-MEA 40, product details.

* cited by examiner

*Primary Examiner* — Audrea Buckley
(74) *Attorney, Agent, or Firm* — Tarter Krinsky & Drogin LLP

(57) ABSTRACT

A method, composition and kit for straightening human hair. The method comprises applying an alkali relaxer to the hair and then neutralizing the hair with a hair neutralizing composition comprising at least one fatty acid or a quaternary derivative thereof. The kit comprises an alkali hair relaxer or components for preparing such a relaxer and the hair neutralizing composition.

11 Claims, No Drawings

NEUTRALIZING HAIR COMPOSITION

TECHNICAL FIELD

The invention relates generally to compositions, kits and methods for straightening hair. More particularly, the invention is directed to neutralization of hair that has been treated with an alkali relaxer wherein fatty acids are used to normalize the pH of the hair.

BACKGROUND OF THE INVENTION

Hair relaxers are used for permanent straightening of curly and/or kinky hair. Such products are used by women of African ancestry. The relaxer is typically an alkali which breaks the natural disulfide bonds within the hair. The user mechanically straightens the hair. Then the disulfide bonds are reformed in the straightened hair through neutralization of the active ingredient in the relaxer, which is often a strong alkali.

The alkali relaxers for which the neutralizing compositions and methods of the present invention are applicable include those comprising a strong alkali. The neutralizing compositions and methods contained within may also work on weak alkali, such as monoethanolamine, triethanolamine, and ammonium hydroxide, which may be used to lessen the degree of curl by weakening the disulfide bonds. These weak alkali, however, are not considered effective enough for use in relaxers. In addition to breaking the disulfide bonds, these types of relaxers also neutralize the fatty acids contained in the hair lipids, thus stripping the fatty acids from the hair.

There are two common types of alkali hair relaxers. The first type is known as a lye relaxer and prime examples contain sodium hydroxide, lithium hydroxide, or potassium hydroxide; the alkali metal hydroxides. These lye relaxers are usually supplied in cream form and are applied directly to the hair. Because of the inherent dangers to hair and skin of sodium hydroxide and other alkali metal hydroxides, lye relaxers are usually relegated to the professional sector of the hair care market.

The second type of alkali relaxer is known as a no-lye relaxer. No-lye relaxers make up the bulk of the non-professional or home use market sector. A no-lye relaxer system comprises a precursor cream which contains an alkaline earth metal hydroxide, such as calcium hydroxide, which is mixed with a liquid activator that contains a strong nitrogenous base, such as guanidine carbonate. The activator liquid and the precursor cream are mixed just prior to use. There is a chemical reaction between these components, for example, between the calcium hydroxide in the precursor cream and the guanidine carbonate in the liquid. This reaction produces the hair relaxing agent in activated form, in this case, guanidine hydroxide, which becomes the active alkali in treating the hair. A lye relaxer does not require a separate activator to produce the active relaxing agent, which is, for example, sodium hydroxide or lithium hydroxide.

All alkali relaxers are meant to be applied to the hair for a specific period of time. Then they are to be rinsed off and thereafter to be neutralized, to stop the action of the relaxer. Neutralizing is typically done using an acidic neutralizing shampoo to bring the hair back to a neutral pH. Typically, the hair is then conditioned with a leave in conditioner.

Relaxing human hair is a destructive and irritating process that is known to strip the hair of its natural fatty acids. Neutralizing shampoos that are typically used after the relaxer can further strip away the fatty acids due to their detergency effect. The hair neutralizing compositions, systems, kits and methods of the present invention avoid at least some damage caused by acidic neutralizing shampoos.

SUMMARY OF THE INVENTION

The present invention relates to a method for straightening human hair. An alkali relaxer, which is preferably embodied in a cream form, is applied to the hair. Then after the hair has been relaxed, the hair is neutralized by applying an amount of a neutralizing composition comprising at least one fatty acid that is effective to neutralize the hair. Fatty acids or natural oils high in fatty acids may be used to normalize the pH of human hair after a hair relaxer treatment. The neutralizing composition may be applied to the relaxed hair before or after the relaxing cream has been rinsed from the hair. The invention also concerns that neutralizing composition and a kit for relaxing and neutralizing the hair.

The amount of fatty acids to be applied to neutralize the hair is here described as effective to neutralize the hair. For each neutralizing composition and each user, that effective amount will vary. The factors that may be considered in selecting an effective amount include one or more of: a) the choice of a fatty acid including its acid value and its similarity to fatty acids naturally present in hair; b) the concentration of the fatty acid in the vehicle used to apply the fatty acid to the hair; c) the quantity of the vehicle and therefore of the composition applied to the hair being neutralized; d) the quantity of relaxer remaining on the hair before it is to be neutralized, including the effect of rinsing of the relaxer from the hair; e) the strength or the pH of the remaining relaxer; f) the period of time during which the neutralizing composition remains in the hair. Other factors not listed may affect the selection of an effective amount. The designer balances all these factors and after testing determines for what period of time a user should apply the particular neutralizing composition to achieve a selected degree of neutralization. Then the effective amount of the neutralizing composition can be specified.

In one embodiment, the fatty acid in the neutralizing composition is a fatty acid normally found in human hair.

In another embodiment, the neutralizing composition comprises a mixture of fatty acids which has a fatty acid distribution that closely matches the distribution of fatty acids contained in human hair.

Suitable fatty acids and/or natural oils high in fatty acids have been substantially characterized with respect to those occurring in human hair. The fatty acids in these oils are an effective neutralizer for the alkali contained in the relaxer, and the fatty acids restore the relaxed, not curled or kinky, hair to a healthier state.

The benefit of neutralizing hair using an effective amount of a fatty acid instead of a shampoo is that the hair becomes neutralized without further stripping away of fatty acids. Furthermore, the neutralizing fatty acid can potentially replace lost fatty acids, leaving the hair softer, stronger and less damaged. The neutralizing fatty acid should be rinsed from the hair after application to avoid a greasy afterfeel.

Effective amounts of fatty acids will have a neutralizing effect if they are alone applied to the hair. But, it is easier to apply effective amounts of these acids when they are part of a vehicle (also referred to herein as a solvent) that aids in more uniform application to the hair. Such a vehicle may be a natural oil which may or may not contain its own fatty acids. A synthetic oil or mineral oil may also be used as a vehicle. Vehicles for delivery of compositions to hair are known in the art.

Hair that has been relaxed and neutralized with a neutralizing shampoo tends to be hydrophilic, which is an unhealthy state for hair. When an effective amount of a fatty acid or a high fatty acid natural oil is used in place of a neutralizing shampoo, the hair is more hydrophobic, which is a more healthy state. A further benefit of applying an effective amount of a fatty acid or a high fatty acid neutralizing oil in place of a neutralizing shampoo is that the neutralizing and conditioning may be all accomplished in one step, as fatty acids have conditioning properties through the process of refatting. This can avoid the two steps typically used currently, neutralizing then conditioning.

In summary, there are multiple purposes for the neutralizing composition of the present invention. The first is to neutralize the residual alkali on the hair. The second is to replenish the fatty acids that were stripped during the relaxing process. The third is to restore the hair's natural hydrophobic state. If the neutralizing composition includes a natural oil that contains fatty acids, the natural oil also functions as a solvent or carrier for applying the other components of the neutralizing composition to the hair.

DETAILED DESCRIPTION OF THE INVENTION

According to an article published in the journal LIPIDS, (Integral Lipids of Human Hair, Wertz and Downing; 1988 Vol. 23, No. 9, pp. 878-881) fatty acids make up the majority of the lipids found in human hair. Among the most prevalent are C16:0 (palmitic), C18:0 (stearic), C18:1 (oleic) and alpha-linoleic. By far the most prevalent fatty acid found in human hair is C21:0 anteiso, which is otherwise known as 18-methyl eicosanoic acid, abbreviated 18-MEA. These and other fatty acids, individually or in combination, may be used as hair neutralizing agents in the practice of the present invention. The use of a natural oil provides a suitable solvent and, if the natural oil has a distribution of fatty acids that provides at least some of the type and quantity of those found in human hair lipids, this is advantageous because it enables restoration of the hair to a state more closely approximating its condition prior to relaxation treatment than would be possible with the use of a single fatty acid. This state may also be referred to as the hair's "natural state". It is possible, by choosing an appropriate natural oil, or a combination of oils, and supplementing the oil or oils with one or more fatty acids to provide an effective amount of a fatty acid to restore the hair to a state closely resembling its natural state.

There are many natural oils high in fatty acid content which may be used as described above, including canola oil, corn oil, flaxseed oil, olive oil, safflower oil, soybean oil, and sunflower oil. Sunflower oil is a good match in terms of cost, availability, and stability. It has a lower oleic acid content than some of the other oils listed, but as oleic acid is a cost effective, easy to use supplement to the sunflower oil in exemplary embodiments of the methods, compositions and kits of the present invention, this is not a problem. The oleic acid functions to bolster the neutralizing effect of the natural oil by providing additional fatty acids and to provide a further source of one of the most abundant fatty acids typically found in human hair. The use of one or more natural oils also provides a good solvent for applying the fatty acids contained therein to the hair.

As has been noted above, the relaxers for which the neutralizing compositions and methods of the present invention are applicable include those comprising a strong alkali. In addition to breaking the disulfide bonds, these types of relaxers also neutralize the fatty acids contained in the hair lipids, thus stripping the fatty acids from the hair. 18-MEA is an unusual long chain fatty acid seldom found naturally outside of mammalian hair. It is found predominantly in a surface layer of the hair's surface, or cuticle, along with palmitic and oleic acids. A quaternized derivative of 18-MEA may be added to the neutralizing composition as a conditioning agent and as a replacement for the 18-MEA that had been stripped from the hair during the relaxing process as is mentioned above. This quaternized version comes in the form of C10-40 Isoalkylamidopropylethyldimonium Ethosulfate. A 40% active version of this quaternized version of 18-MEA (in the solvent Dipropylene Glycol) exists as "Cutissential 18-MEA 40", a proprietary item from Croda Chemicals.

The neutralizing composition may also include an acidic oil soluble surfactant to aid in rinsing of the neutralizing composition from the hair. An example of such a surfactant is lauroyl sarcosine. The lauroyl sarcosine is an acid precursor to sodium lauroyl sarcosinate, a cleansing surfactant commonly found in shampoos and body washes. It is an oil-soluble, acidic surfactant that fits well and is chemically compatible with the other components of the formula, and aids in the rinse off of the product from the hair. Other surfactants known in the art may work as well, in providing the aid in rinsing off the product from the hair.

A fragrance and an antioxidant to prevent long term rancidity of the natural oil may optionally also be added to the above exemplary formulation. Suitable antioxidants include tocopherol acetate and BHT. As discussed above, other oils and fatty acids may be substituted for the sunflower oil and oleic acid and other surfactants may be substituted for the lauroyl sarcosine.

A non limiting exemplary formulation of an effective amount of a neutralizing composition of the present invention including for use in a kit and for practicing a method of the present invention is as follows:

Example 1

| Ingredient | Range (% by weight) |
| --- | --- |
| sunflower oil | 0-100 |
| oleic acid | 0-100 |
| Cutissential ™ 18-MEA 40 | 0-20 |
| lauroyl sarcosine | 0-5 |

Example 2

Another exemplary specific embodiment of suitable components in the present invention is as follows including an effective amount of a neutralizing composition of the invention is:

(a) sunflower oil, 68.0%
(b) oleic acid, 30%
(c) $C_{10-40}$ Isoalkylamidopropylethyldimonium Ethosulfate (and) Dipropylene Glycol, (component (c) is the INCI (International Nomenclature of Cosmetic Ingredients) name of a Croda Incorporated conditioning ingredient named Cutissential™ 18-MEA), 1.0%
(d) lauroyl sarcosine 1.0%
(e) a fragrance
(f) an antioxidant Sunflower oil is obtained from Arista Industries; oleic acid is obtained as Emersol 213™ from Emery Oleochemicals; and lauroyl sarcosine is obtained as Crodasinic L from Croda Chemicals. Cutissential™ 18-MEA-40 is a mixture of $C_{10-40}$ isoalkylamidopropylethyldimonium ethosulfate (a quaternized derivative of 18-methyl eicosanoic acid) and dipropylene glycol available from Croda Inc., Edison N.J.

The following exemplary formulations are designed to include an effective amount of fatty acids and to produce similar fatty acid distributions to the formulation of Example 1 and to more closely match the distribution of fatty acids in human hair.

Example 3

|   | Ingredient | Percentage (by weight) |
|---|---|---|
| A. | Canola Oil | 73.5 |
|   | Flaxseed Oil | 15.0 |
|   | Palmitic Acid | 10.0 |
|   | Cutissential ™ 18-MEA 40 | 1.0 |
|   | Lauroyl Sarcosine | 0.5 |
| B. | Almond Oil | 78.5 |
|   | Flaxseed Oil | 10.0 |
|   | Palmitic Acid | 10.0 |
|   | Cutissential ™ 18-MEA 40 | 1.0 |
|   | Lauroyl Sarcosine | 0.5 |
| C. | Corn Oil | 73.5 |
|   | Oleic Acid | 25.0 |
|   | Cutissential ™ 18-MEA 40 | 1.0 |
|   | Lauroyl Sarcosine | 0.5 |

In examples 3A and 3B, the flaxseed oil serves as the source for linoleic and linolenic acids, which are lacking in the predominant oils. The three formulations of 3A, 3B and 3C illustrate that various combinations of natural oils and fatty acids can be used to achieve an effective amount of a desired fatty acid distribution. Accordingly, this should enable preparation of formulations having fatty acid distributions that closely match the distributions in effective amounts that are present in natural human hair prior to a relaxation treatment.

The embodiments herein may be more generally described.

In one embodiment, the composition comprises an effective amount of at least one fatty acid for neutralizing hair which has been straightened with an alkali relaxer. In another embodiment, the composition comprises one or more natural oils, which are high in fatty acids, providing an effective amount of fatty acid for neutralizing the alkali-relaxed hair.

In a further embodiment, the composition comprises an effective amount of one or more fatty acids in combination with one or more natural oils chosen so that the amount of total fatty acid is sufficient to neutralize any alkali relaxer in the hair, and so that the overall fatty acid distribution of the combined natural oils and fatty acids resembles that found in natural hair.

In another embodiment, the composition comprises a combination of an effective amount of one or more fatty acids with one or more natural oils, and a conditioning agent in the form of a quaternized derivative of 18-methyl eicosanoic acid, which is the primary fatty acid found in natural hair. This conditioning agent may be C10-40 Isoalkylamidopropylethyldimonium Ethosulfate, obtained as a 40% active solution in the solvent Dipropylene Glycol, under the tradename "Cutissential 18-MEA 40" from Croda Chemicals.

In another embodiment, the composition comprises the combination of an effective amount of fatty acid(s) and natural oil(s) along with the quaternized 18-MEA derivative conditioning agent and an acidic, oil-soluble surfactant to aid in rinsing; a fragrance and antioxidant to preserve the stability of the composition.

In a specific embodiment of the method and the composition of the present invention, the neutralizing composition comprises:

(a) a natural oil high in fatty acids;
(b) a fatty acid;
(c) a) and b) together providing an effective amount of fatty acid;
(d) a quaternized derivative of 18-methyl eicosanoic acid;
(e) an acidic oil soluble surfactant;
(f) a fragrance; and
(g) an antioxidant.

In a preferred embodiment of the method and the composition of the present invention, the neutralizing composition comprises:

(a) sunflower oil (Helianthus Anuus Seed Oil);
(b) oleic acid;
(c) a) and b) together providing an effective amount of fatty acid;
(d) $C_{10-40}$ Isoalkylamidopropylethyldimonium Ethosulfate (and) Dipropylene Glycol;
(e) lauroyl sarcosine;
(f) a fragrance; and
(g) an antioxidant.

In the compositions discussed above, the percentage amounts of the surfactant, fragrance and antioxidant components fall within typical ranges of such components found in commercially available hair care products, and the percentage amounts of the natural oil and fatty acid should provide effective amounts for the purpose thereof, i.e., sufficient fatty acid for relaxer neutralization, and sufficient oil to provide a vehicle for applying the other components to the treated hair. If the composition includes a natural oil high in fatty acids as well as additional fatty acid, the total amount of fatty acid present should be sufficient for relaxer neutralization.

The time of treatment for straightening a subject's hair with an alkali relaxer is typically within a range of 5 minutes to 45 minutes. After the time for treatment has elapsed, the hair should be neutralized in order to avoid potential damage or adverse effects to the subject's hair. The relaxing agent mixture may be removed by a thorough rinsing of the subject's hair with water. The rinse is typically followed by a neutralizing step, which may be accomplished by the application of an effective amount of a neutralizing composition, as described above.

Alternatively, after applying the relaxer for a selected period of time and prior to rinsing the relaxer, apply the neutralizing composition to the hair and then rinse off the neutralized relaxer and any remaining residual relaxer along with remaining neutralizing composition from the hair.

As a further alternative, the hair may be treated with an effective amount of a neutralizing composition and then rinsed, optionally followed by a second application of an effective amount of neutralizing composition. This alternative procedure allows for neutralization of the alkali relaxer before the introduction of additional water. There is evidence that some of the damage resulting from alkali relaxers comes during the rinsing of the relaxer cream, when water can easily enter into hair in a swollen state. The ability to neutralize the relaxer in the absence of water, allowing the hair shaft to de-swell, could help to prevent irreversible cuticle damage.

The neutralizing compositions discussed above are compatible with all alkaline relaxers currently on the market. Following the first procedure set forth above, the consumer or stylist applies the relaxer as normal, lets the relaxer sit for the appropriate amount of time—as normal, and then rinses the relaxer completely from the hair—again as she or he normally would. The consumer or stylist then immediately and thoroughly applies the neutralizing composition to all parts of the hair that had been contacted by the relaxer. After letting the composition sit for 10 to 20 seconds the composition is then rinsed from the hair. While care must be taken to saturate all relaxed hair, there is no problem with the composition coming into contact with the scalp or unrelaxed hair. The process of the invention is now finished. The hair can be further shampooed or conditioned if desired. Thus, the neutralizing composition may take the place of the neutralizing shampoo or neutralizing conditioner that is supplied with many relaxers or by salons.

The present invention also relates to a kit for straightening human hair comprising an alkali hair relaxer or components necessary for preparing such a relaxer and a hair neutralizing composition comprising a an effective amount of fatty acid. The fatty acid is preferably a fatty acid normally found in human hair or a quaternary derivative thereof. In another embodiment, the kit comprises an alkali hair relaxer or components required for preparing such a relaxer and a hair neutralizing composition comprising a natural oil high in fatty acids to provide an effective amount of such acids.

The kit alternatively comprises an alkali hair relaxer or components for preparing such a relaxer and also comprises a hair neutralizing composition selected from those described above.

Although the present invention has been described in relation to particular embodiments thereof, many other variations and modifications and other uses will become apparent to those skilled in the art. The present invention should, therefore, not be limited by the specific disclosure herein, but only by the appended claims.

What is claimed:

1. A method of straightening human hair, the method comprising the steps of:
    (a) applying an alkali relaxer to the hair to relax the hair; and
    (b) applying at least one fatty acid to the hair in a predetermined amount sufficient to stop the relaxing of the hair by the alkali relaxer.

2. The method according to claim 1, further comprising rinsing off the relaxer before applying the fatty acid to the hair.

3. The method of claim 1, wherein the predetermined amount of fatty acid comprises using one or more of the following factors: (a) the choice of a fatty acid including its acid value and its similarity to fatty acids naturally present in hair; (b) the concentration of the fatty acid in the vehicle used to apply the fatty acid to the hair; (c) the quantity of the vehicle and therefore of the composition applied to the hair being neutralized; (d) the quantity of relaxer remaining on the hair before it is to be neutralized, including the effect of rinsing of the relaxer from the hair; (e) the strength or the pH of the remaining relaxer; or (f) the period of time during which the neutralizing composition remains in the hair.

4. The method of claim 1, wherein the fatty acid is a fatty acid normally found in human hair.

5. The method of claim 1, wherein the fatty acid is present in a natural oil.

6. The method of claim 1, further comprising contacting the hair with a conditioner.

7. The method of claim 6, wherein the conditioner is a quaternized derivative of 18-methyl eicosanoic acid.

8. The method of claim 7, wherein the quaternized derivative is C10-40 Isoalkylamidopropylethyldimonium Ethosulfate.

9. The method of claim 1, wherein the fatty acid is selected from the group consisting of
    palmitic, stearic, oleic and alpha-linolenic acid.

10. The method of claim 1, further comprising applying
    at least one additional fatty acid to the hair.

11. The method of claim 1, further comprising the step of applying the fatty acid to the hair prior to rinsing the relaxer, then rinsing off any remaining residual relaxer from the hair.

* * * * *